(12) United States Patent
Burghardt

(10) Patent No.: US 9,538,786 B2
(45) Date of Patent: Jan. 10, 2017

(54) INHALATION DEVICE

(75) Inventor: Thorsten Burghardt, Castrop-Rauxel (DE)

(73) Assignee: S.A.S.C. AG, Baar (CH)

( * ) Notice: Subject to any disclaimer, the term of this patent is extended or adjusted under 35 U.S.C. 154(b) by 676 days.

(21) Appl. No.: 13/983,852

(22) PCT Filed: Feb. 6, 2012

(86) PCT No.: PCT/EP2012/051981
§ 371 (c)(1),
(2), (4) Date: Aug. 6, 2013

(87) PCT Pub. No.: WO2012/107414
PCT Pub. Date: Aug. 16, 2012

(65) Prior Publication Data
US 2013/0312777 A1 Nov. 28, 2013

(30) Foreign Application Priority Data
Feb. 7, 2011 (DE) .................. 10 2011 010 532

(51) Int. Cl.
*A24F 47/00* (2006.01)
*A61M 15/06* (2006.01)
*A61M 15/00* (2006.01)

(52) U.S. Cl.
CPC ........ *A24F 47/002* (2013.01); *A61M 15/0028* (2013.01); *A61M 15/0031* (2014.02); *A61M 15/0043* (2014.02); *A61M 15/06* (2013.01)

(58) Field of Classification Search
CPC ........ A24F 47/00; A24F 47/002; A61M 15/06
See application file for complete search history.

(56) References Cited

U.S. PATENT DOCUMENTS

| | | |
|---|---|---|
| 5,167,242 A | 12/1992 | Turner et al. |
| 5,400,808 A | 3/1995 | Turner et al. |
| 5,501,236 A | 3/1996 | Hill et al. |
| 6,098,632 A | 8/2000 | Turner et al. |
| 2005/0016550 A1 | 1/2005 | Katase |
| 2006/0130857 A1 | 6/2006 | Roth et al. |
| 2006/0188128 A1 | 8/2006 | Rhoads |

FOREIGN PATENT DOCUMENTS

| | | | |
|---|---|---|---|
| CN | 1059649 A | | 3/1992 |
| CN | 2853083 Y | * | 1/2007 |
| DE | 103 21 379 A1 | | 12/2004 |
| GB | 409 650 A | | 3/1934 |

(Continued)

OTHER PUBLICATIONS

Machine Translation of CN2853083Y. Published Jan. 3, 2007.*

(Continued)

*Primary Examiner* — Jason L Lazorcik
*Assistant Examiner* — Cynthia Szewczyk
(74) *Attorney, Agent, or Firm* — Collard & Roe, P.C.

(57) ABSTRACT

A refillable device for the inhalation of gaseous media, particularly nicotine, the device consisting of a sleeve-shaped body in which a depot carrier is arranged. The depot carrier receives a depot which is sealed in a gas-tight manner. A mouth piece is arranged downstream of the depot in the suction direction, and there is an activation device for opening the depot.

7 Claims, 18 Drawing Sheets

(56) References Cited

FOREIGN PATENT DOCUMENTS

Figure 1:
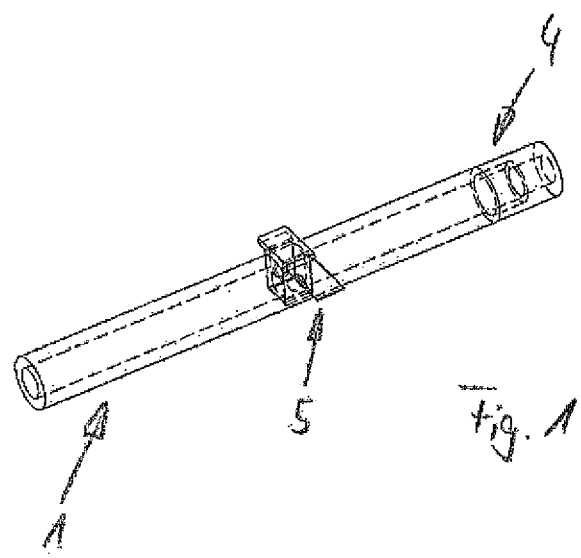

| JP | H05-507639 A | 11/1993 |
|---|---|---|
| JP | 2006-223158 A | 8/2006 |
| WO | WO 2006/002445 A2 | 1/2006 |
| WO | WO 2007/090594 A1 | 8/2007 |

OTHER PUBLICATIONS

International Search Report of PCT/EP2012/051981, date of mailing Jun. 25, 2012.
International Preliminary Report on Patentability of PCT/EP2012/051981, Jul. 8, 2013.

* cited by examiner

INHALATION DEVICE

CROSS REFERENCE TO RELATED APPLICATIONS

This application is the National Stage of PCT/EP2012/051981 filed on Feb. 6, 2012, which claims priority under 35 U.S.C. §119 of German Application No. 10 2011 010 532.8 filed on Feb. 7, 2011, the disclosure of which is incorporated by reference. The international application under PCT article 21(2) was not published in English.

The invention relates to an apparatus for inhalation of gaseous media, particularly nicotine, which apparatus consists of a sleeve-shaped body that accommodates a depot that is sealed in gas-tight manner, and which apparatus has a mouthpiece disposed behind the depot in the suction direction, as well as an activation device for opening the depot.

There are a great number of application cases for inhalation of gaseous media. In the medical and therapeutic sector, in particular, inhalation of gases finds many different uses. However, smoking is also one of the application cases in which a gaseous medium is inhaled. In this connection, commercially available cigarettes generally consist of tobacco rolled up in paper or a tobacco leaf, as well as a filter element affixed on a mouthpiece. By means of igniting the front end of the cigarette, the tobacco burns at its glow point or carbonizes, and releases nicotine, which is entrained by the smoke to be inhaled by the smoker. During combustion at glow point or carbonization of the tobacco, not only nicotine but also other substances are released or produced, which are frequently harmful to health, such as tar, compounds that contain arsenic and cadmium, as well as carcinogenic compounds such as hydrazine, chrysene, formaldehyde, nitrosamines, and the like.

For some time, attempts have been made to establish what are called smoke-free cigarettes on the market. These are products in which the tobacco is merely heated, without being burnt, so that the desired nicotine is supposed to be released, but the formation of substances harmful to health is avoided. A further approach for a smoke-free cigarette is described in DE 103 21 379 A1. In the case of this smoke-free cigarette, air is heated using an electrical heating device, and the heated air is passed through a disposable depot, in which a predetermined amount of nicotine is accommodated. The nicotine is supposed to be released by the heated air and inhaled by the user.

Because it is complicated to place an electrical heating device in the smoke-free cigarette, a smoke-free cigarette has been developed that contains a disposable depot in which a carrier substance for the nicotine is provided, which substance releases the nicotine at ambient temperatures (cf. WO 2007/090594 A1). In this connection, the depot is sealed in gas-tight manner and is opened using an activation device, when needed, so that the gas provided in the depot can be inhaled. Furthermore, a nicotine-impenetrable container as well as a method for its production are known from U.S. Pat. No. 6,098,632 A.

The known smoke-free cigarette fulfills the demands made on it. However, its structure is very complex, and therefore its handling is complicated. Furthermore, it is disadvantageous that refilling after use is only possible with great restrictions.

This is where the invention wants to provide a remedy. The invention is based on the task of creating an apparatus for inhalation of gaseous media, particularly nicotine, in which reliable functioning is guaranteed and which can be used multiple times. According to the invention, this task is accomplished by the features of claim 1.

With the invention, an apparatus for inhalation of gaseous media, particularly nicotine, has been created, which guarantees reliable functioning with fewer components, and which can be used multiple times. Furthermore, the apparatus includes the advantages of healthy smoking known from the state of the art.

A depot carrier that is removable is preferably disposed in the body. The depot carrier is able to accommodate the depot that is filled with the gaseous medium. Because of its removability, replacement of the depot is possible in simple manner, and this facilitates refilling.

A particular embodiment consists in forming an accommodation in the body. The accommodation can accommodate the depot directly, and this simplifies the structure of the apparatus.

Alternatively, the accommodation can accommodate the depot carrier, which facilitates handling of the apparatus.

In a further development of the invention, the activation device is formed by a film. Use of a film as the activation device offers the advantage of a space-saving and inexpensive configuration.

It is advantageous if the film is self-adhesive. The use of a self-adhesive film leads to advantages in handling in connection with the production of the smoke-free cigarette or of the depot carriers.

In another further development of the invention, the activation device comprises a pull-off apparatus. Using the pull-off apparatus, activation of the cigarette and therefore handling of the cigarette before consuming it is possible in simple and very convenient manner.

In an embodiment of the invention, the pull-off apparatus has a lay-down part. Use of the lay-down part allows placement of the pull-off apparatus on the smoke-free cigarette, with precise fit.

Preferably, a handle piece is disposed on the lay-down part. In this way, handling of the cigarette during activation is additionally facilitated.

In another embodiment of the invention, the handle piece can be folded away. The use of a fold-away handle piece allows space-saving placement of multiple depots, for example in a box.

The activation device is extremely preferably formed by at least one cutting blade. Using the cutting blade, activation for use of the cigarette is possible in simple and, at the same time, reliable manner, by means of puncturing the seal that is provided.

Figure 2:
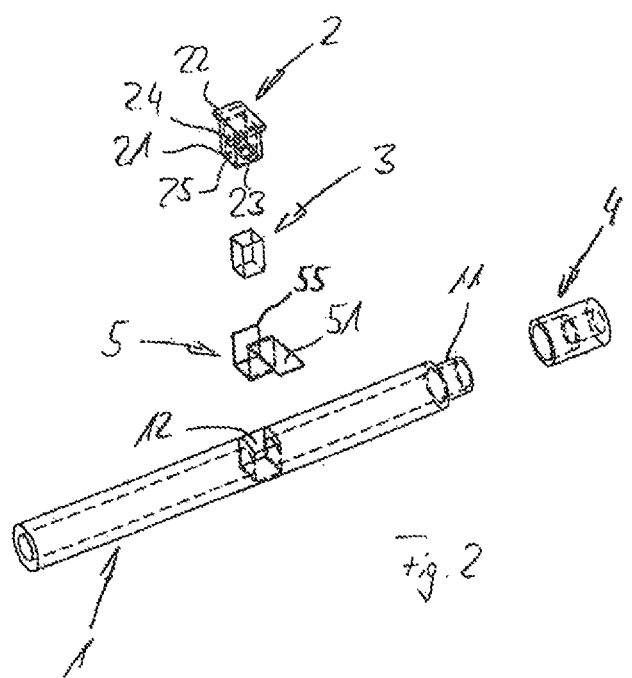
Figure 3:
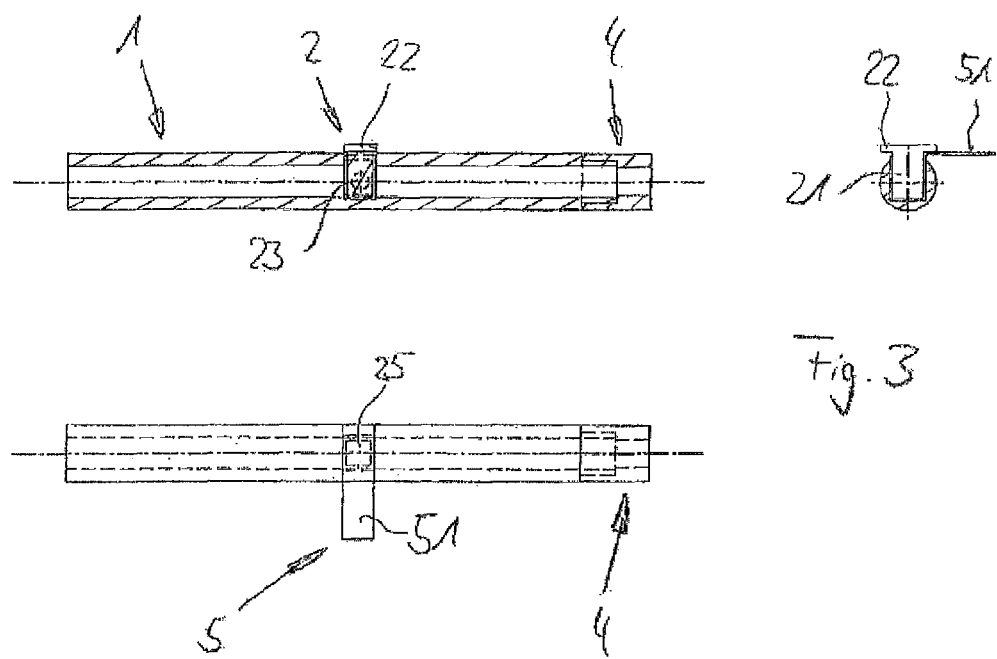
Figure 4:
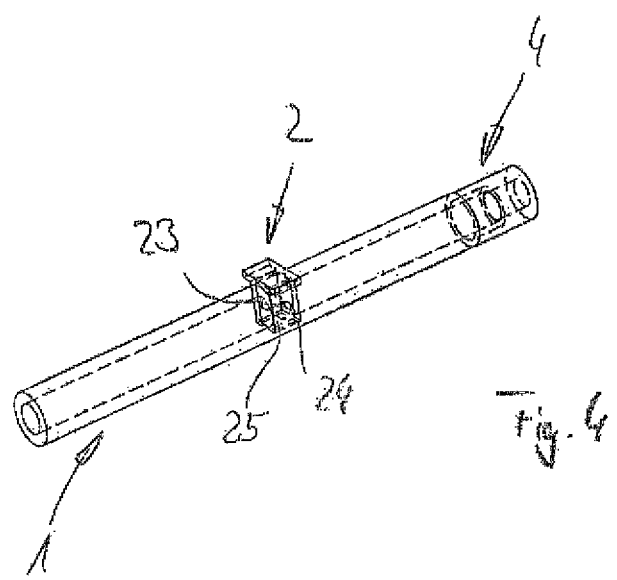
Figure 5:
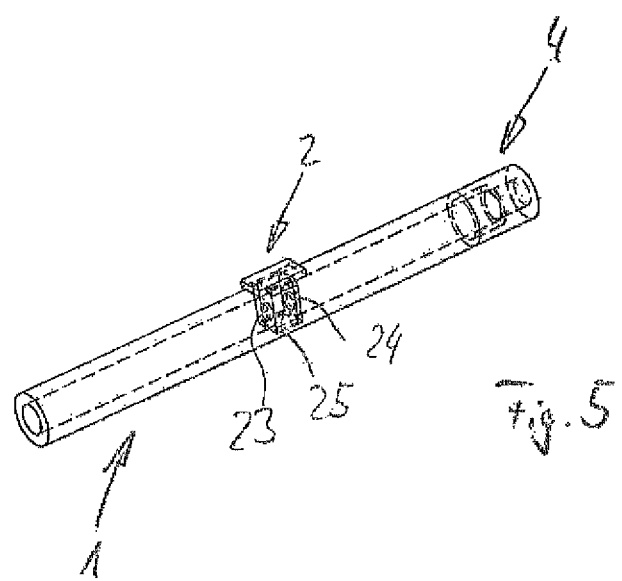
Figure 6:
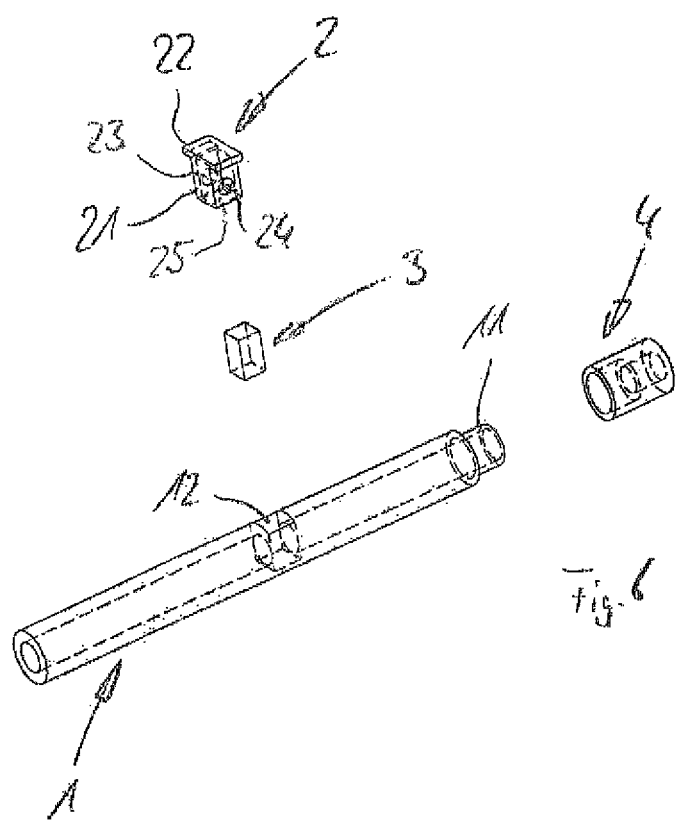
Figure 7:
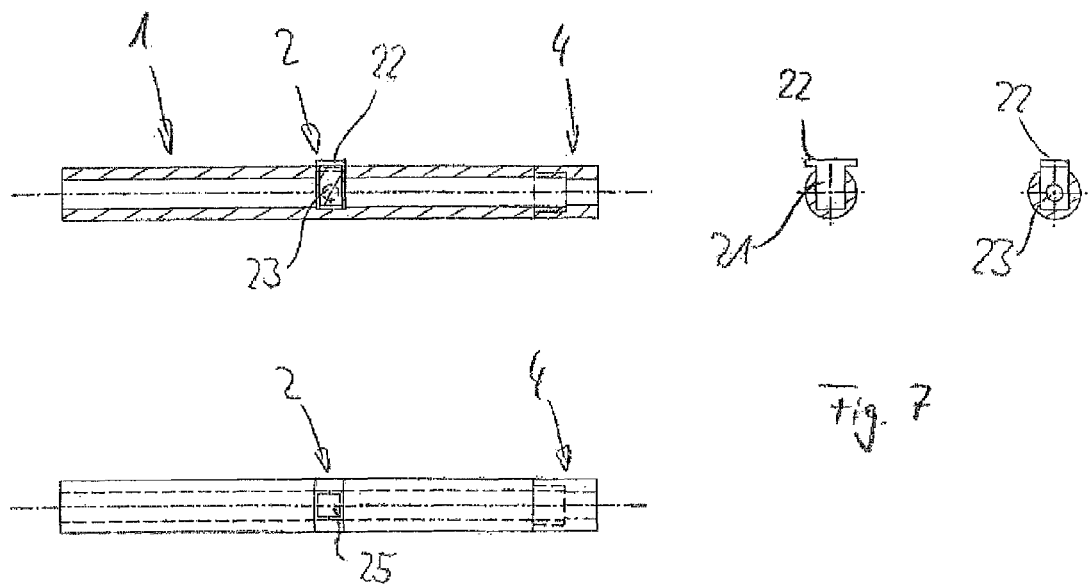
Figure 8:
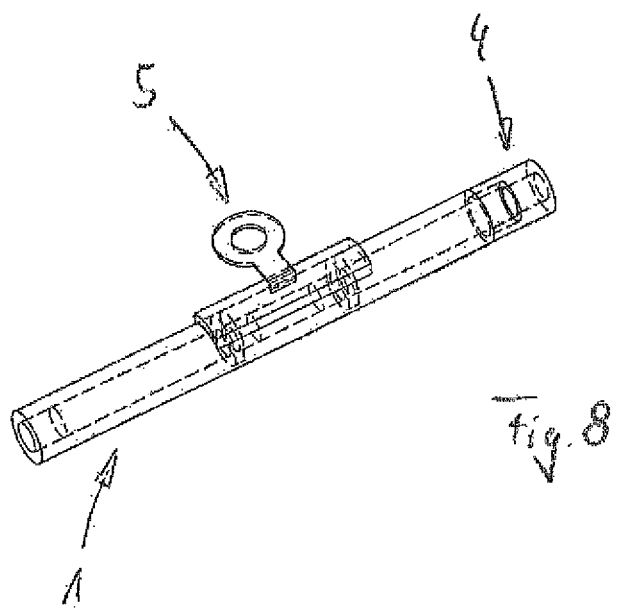
Figure 9:
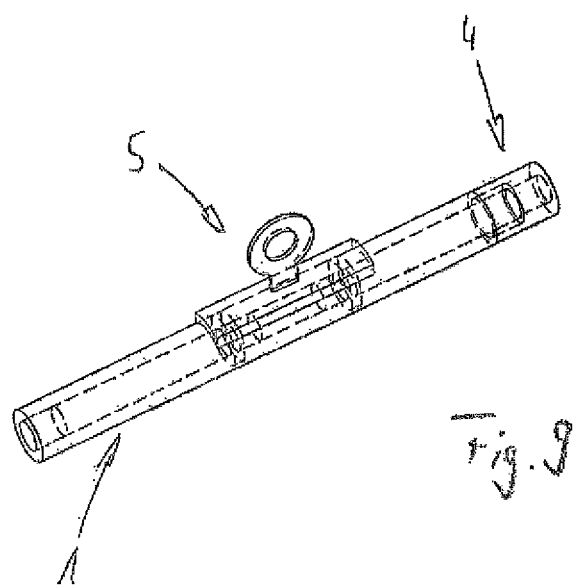
Figure 10:
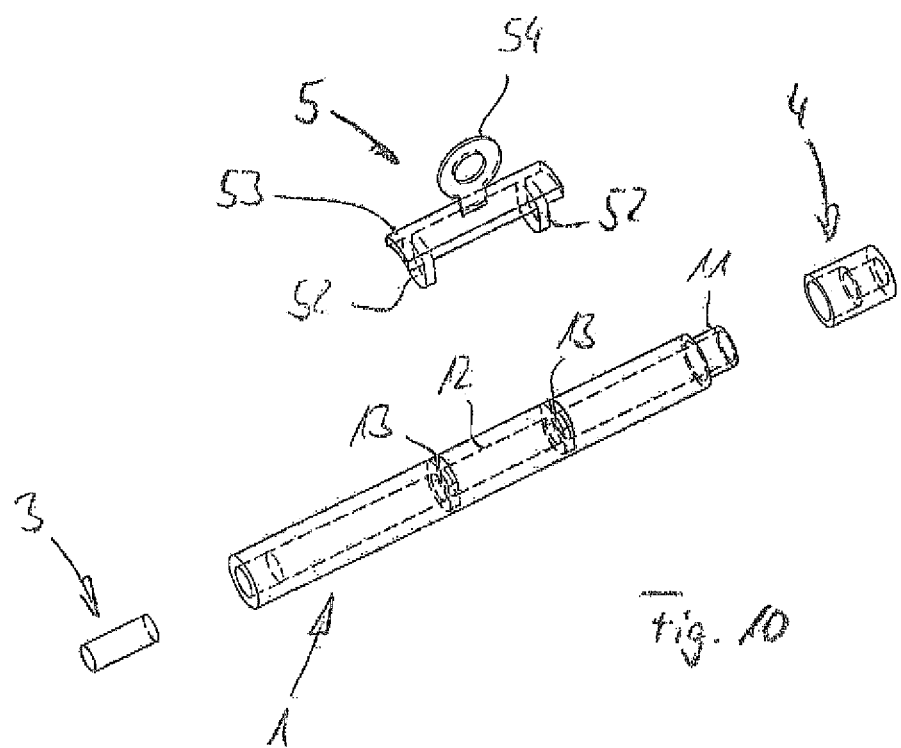
Figure 11:
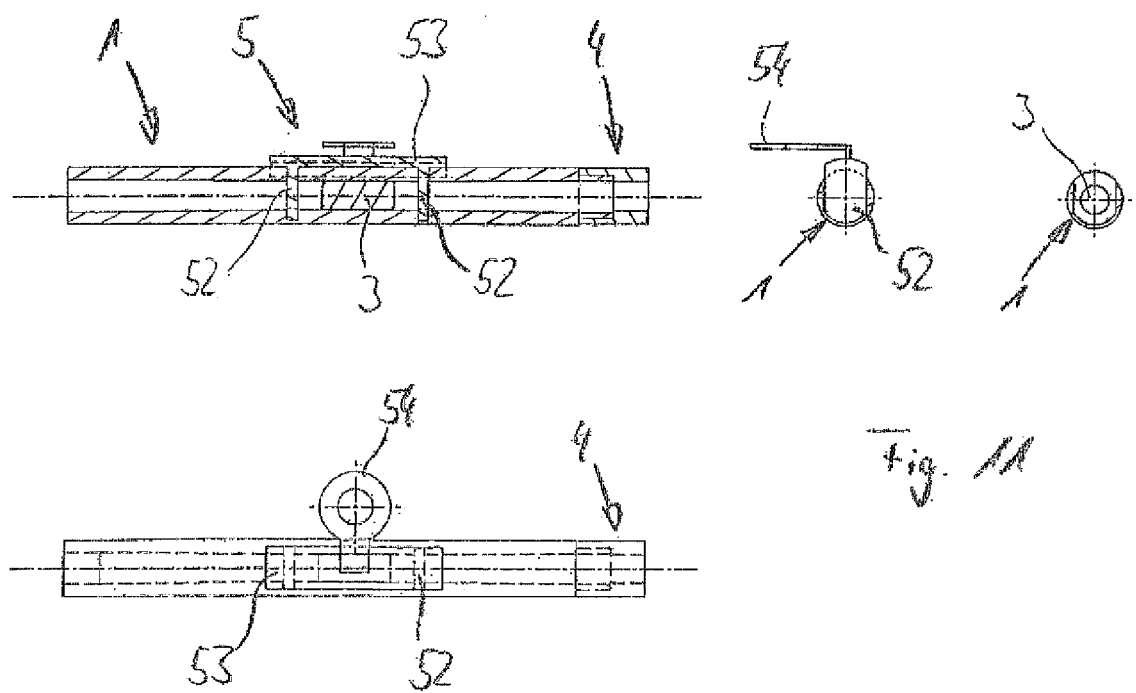
Figure 12:
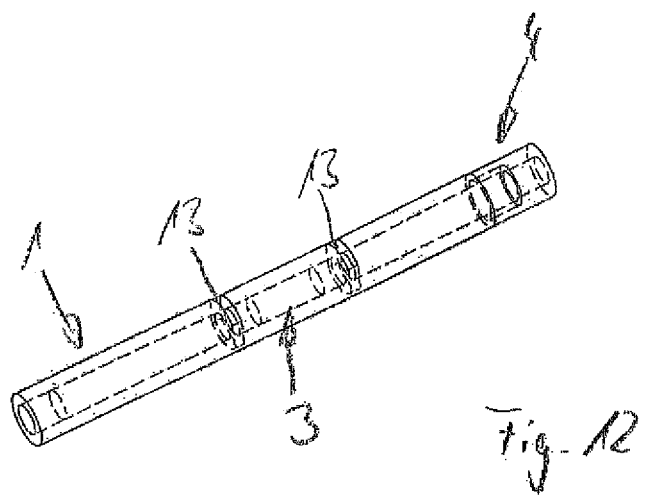
Figure 13:
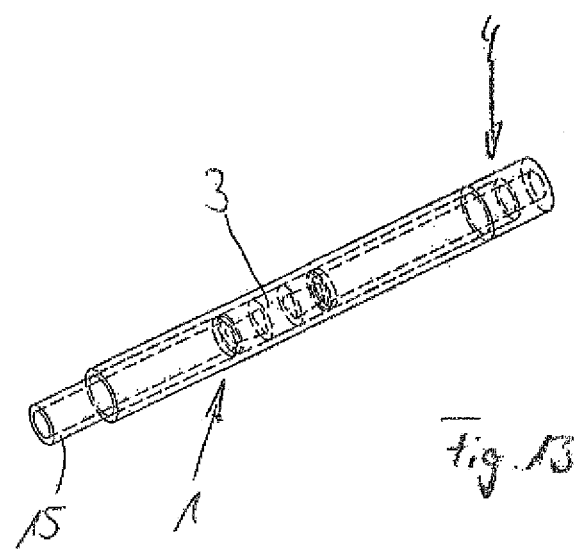
Figure 14:
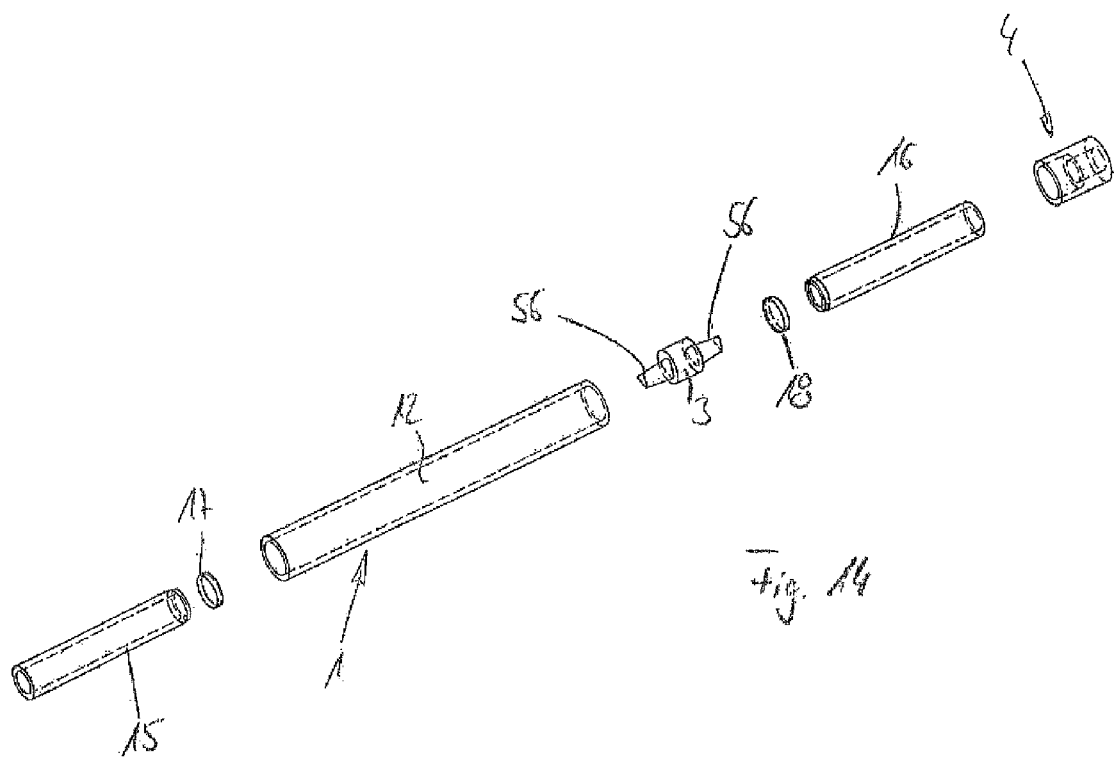
Figure 15:
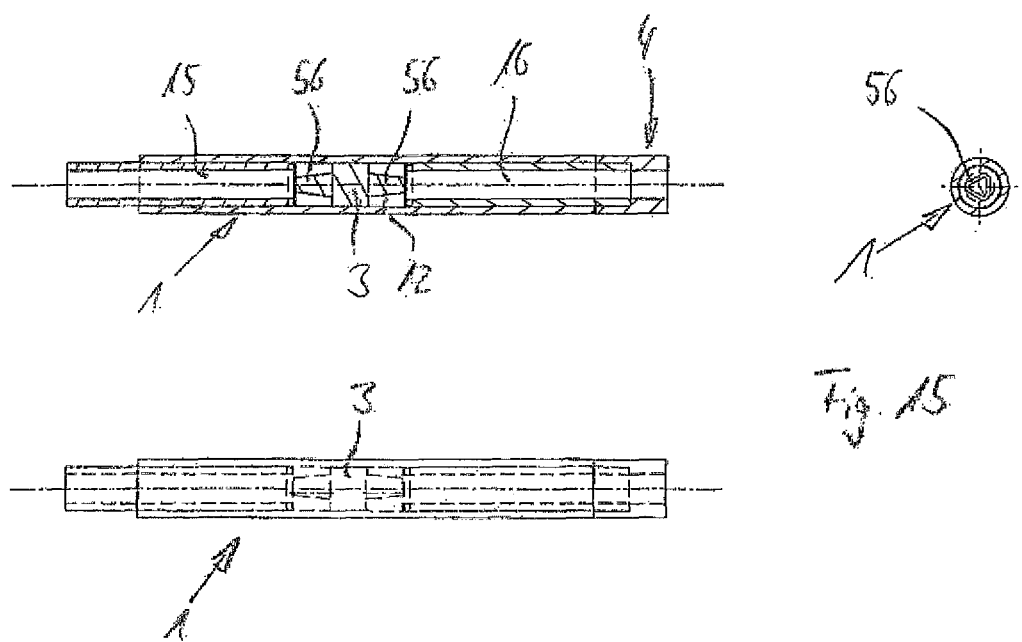
Figure 16:
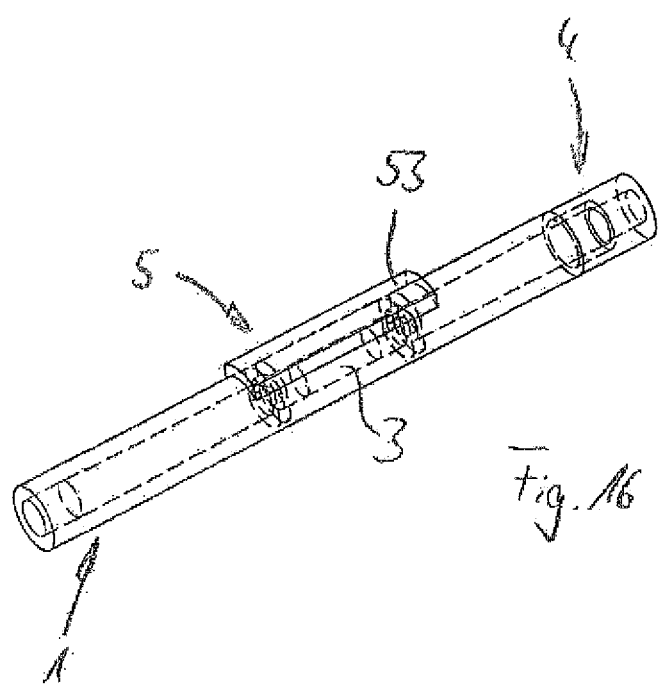
Figure 17:
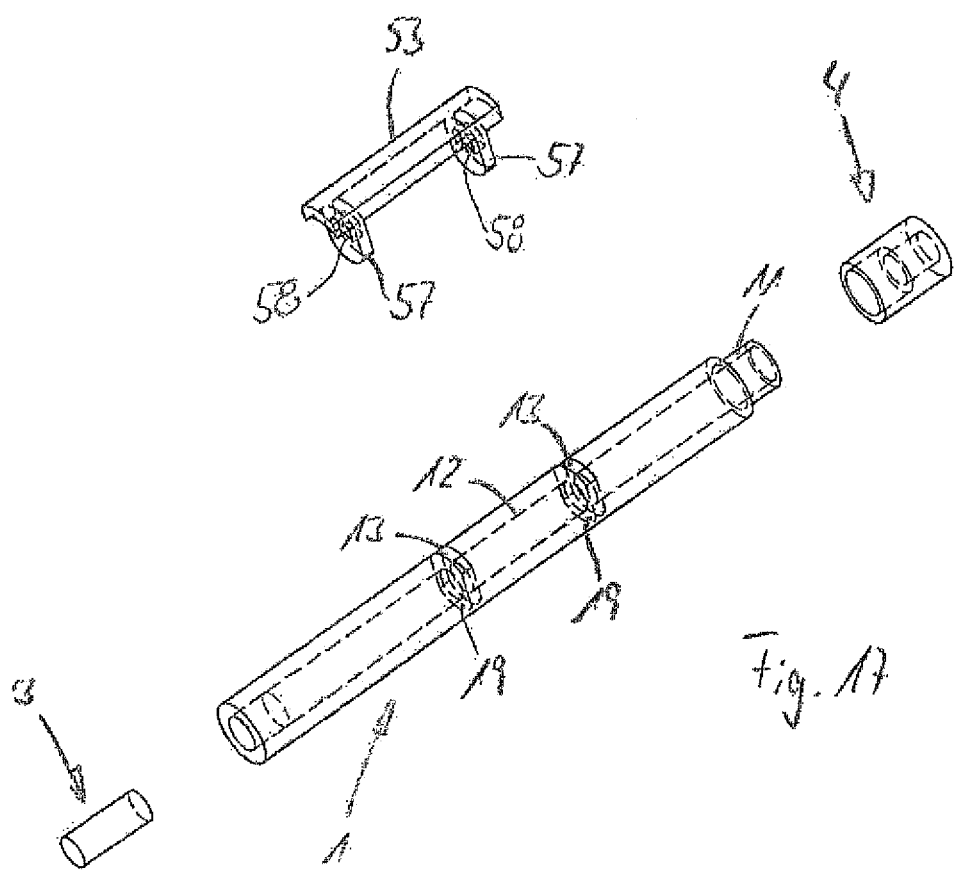
Figure 18:
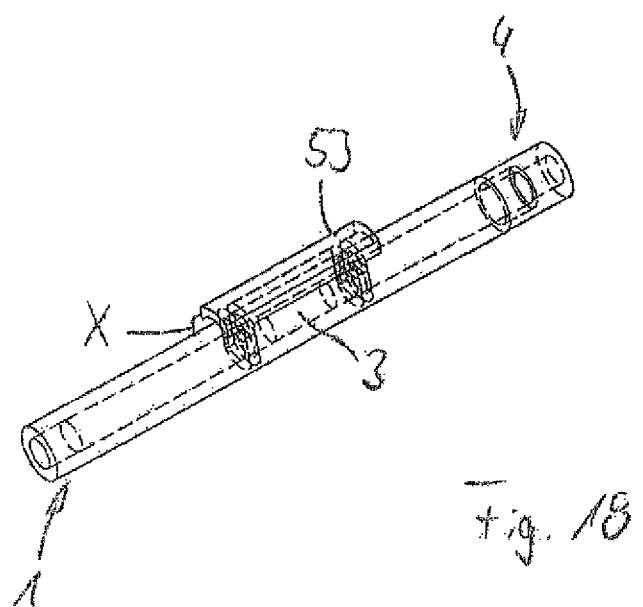

Other further developments and embodiments of the invention are indicated in the other dependent claims. An exemplary embodiment of the invention is shown in the drawing and will be described in detail below. The figures show:

FIG. 1 the perspective representation of a smoke-free cigarette in a first embodiment;

FIG. 2 the exploded representation of the smoke-free cigarette shown in FIG. 1;

FIG. 3 various sectional representations of the smoke-free cigarette shown in FIG. 1;

FIG. 4 the perspective representation of a smoke-free cigarette in a second embodiment, in a position not ready for use;

FIG. 5 the perspective representation of the smoke-free cigarette shown in FIG. 4, in a position ready for use;

FIG. 6 the exploded representation of the smoke-free cigarette shown in FIG. 4;

FIG. 7 various sectional representations of the smoke-free cigarette shown in FIG. 4;

FIG. 8 the perspective representation of a smoke-free cigarette in a third embodiment, with a folded-away handle piece;

FIG. 9 the smoke-free cigarette shown in FIG. 8, with the handle piece in the activation position;

FIG. 10 the exploded representation of the smoke-free cigarette shown in FIG. 8;

FIG. 11 various sectional representations of the smoke-free cigarette shown in FIG. 8;

FIG. 12 the perspective representation of the sleeve-shaped body of the exemplary embodiment according to FIG. 8;

FIG. 13 the perspective representation of a smoke-free cigarette in a fourth embodiment;

FIG. 14 the exploded representation of the smoke-free cigarette shown in FIG. 13;

FIG. 15 various sectional representations of the smoke-free cigarette shown in FIG. 13;

FIG. 16 the perspective representation of a smoke-free cigarette in a fifth embodiment;

FIG. 17 the exploded representation of the smoke-free cigarette shown in FIG. 16;

FIG. 18 the perspective representation of the smoke-free cigarette shown in FIG. 16, in a position ready for use.

The apparatus selected as an exemplary embodiment, for inhalation of gaseous media, particularly nicotine, consists of a sleeve-shaped body 1. A depot 3 is disposed in the body 1. The apparatus has a mouthpiece 4 disposed behind the depot 3 in the suction direction, as well as an activation device 5 for opening the depot 3. The apparatus is refillable.

In the exemplary embodiment, the body 1 is produced from cardboard. In a modification of the exemplary embodiment, other materials, such as plastic or metal, for example, can also be used. The body 1 is configured to be open at its two ends. At one of its ends, a cylindrical step 11 is provided, which serves for setting on the mouthpiece 4. In the center region of the body 1, an accommodation 12 is furthermore configured, into which a depot carrier 2 can be set in the exemplary embodiments according to FIGS. 1 to 7; in the other exemplary embodiments, the accommodation 12 accommodates the depot 3 directly.

The accommodation 12 can have various shapes, which are selected as a function of the shape of the depot carrier 2 or of the depot 3 that is used, so that the depot carrier 2 or the depot 3 and the accommodation 12 correspond to one another without problems. For this reason, the accommodation 12 in the exemplary embodiment according to FIGS. 1 to 7 has a square basic shape; in the exemplary embodiment according to FIGS. 8 to 18, in contrast, the accommodation 12 has a cylindrical shape.

In the exemplary embodiment, the depot carrier 2 is also made of cardboard. Here, too, use of other materials, such as plastic or metal, for example, is possible. The use of these materials allows re-use of the depot carrier 2 after consumption of the content of the depot. As was already mentioned above, the shape of the depot carrier 2 corresponds to the shape of the accommodation 12 of the body 1. Likewise, the shape of the depot 3 corresponds to the shape of the depot carrier 2. The depot carrier 2 consists of a block-shaped basic body 21 that is provided with a handle plate 22 at its one-upper-end, which plate projects beyond the basic body 21 on two sides. The basic body 21 is configured to be hollow and has circular openings 23 and 24 on two sides, which openings align with one another. The depot 2 has no bottom on its underside, thereby causing a further opening 25 to be brought about. The depot 3, which is also block-shaped in this embodiment, can then be inserted into the block-shaped basic body 21 through the opening 25.

The depot 3 is a relatively shape-stable body composed of sintered material. Alternatively, nonwoven fabrics or fiber-like materials can also be used. The material is gas-permeable and air-permeable. The depot 3 can have different three-dimensional shapes, for example the shape of a block, cylinder, ellipsoid, a sphere or the like. It is filled with the gaseous medium required for the case of application, in each instance. In the case of use of the apparatus as a smoke-free cigarette, the depot 3 is filled with a gas that contains nicotine.

In the exemplary embodiment according to FIGS. 1 to 3, the activation device is formed by a self-adhesive film 55 that surrounds the opening 25 on the underside as well as the two sides provided with the openings 23 and 24. After the foil 55 is applied, the depot 3 is sealed in gas-tight manner. In this exemplary embodiment, the activation device 5 comprises a pull-off apparatus in the form of a tab 51. As can be derived from the figures, the tab 51 projects laterally beyond the handle plate 22 of the depot carrier 2, so that simple handling is guaranteed.

In the exemplary embodiment according to FIGS. 4 to 7, the depot carrier 2 is configured comparably to the one in FIGS. 1 to 3. It differs only in that it has a slightly enlarged circumference, in comparison, so that after it has been inserted into the accommodation 12, it is positioned under a press fit there, thereby creating an arrangement that is essentially already gas-tight. In addition, the activation device 5 can be formed by an ultra-thin barrier layer that is injected immediately before the depot carrier 2 is inserted into the accommodation 12. After the depot carrier 2 is inserted, the barrier layer hardens, so that the region is sealed in gas-tight manner. In this connection, the barrier layer is preferably formed from wax or oil. Reliable hardening and sealing of the transition between accommodation 12 and the basic body 21 are important in connection with the selection of the material for the barrier layer.

In the exemplary embodiment according to FIGS. 8 to 12, the depot 3 is configured in the manner of a cylinder. In this exemplary embodiment, the accommodation 12 therefore has a circular cross-section. The accommodation 12 is delimited by slots 13 that are provided in the body 1 at a right angle to its longitudinal center line, and correspond with the activation device 5. For this purpose, the activation device 5 is provided with disk-shaped sealing elements 52 that move into the slots 13 in the assembled state. The sealing elements 52 are disposed on an activation part 53 that has a slightly domed shape. The activation part 53 therefore lies closely against the shape of the body 1 in the assembled state. A handle piece 54 is disposed on the activation part 53, which piece can be folded away. In the exemplary embodiment, this is made possible by providing a film hinge. In this exemplary embodiment, sealing therefore takes place using the clamping that prevails between the slots 13 and the sealing elements 52, which already brings about sufficient sealing. In addition, however, the possibility exists here, too, of injecting a barrier layer immediately before insertion of the sealing elements 52 into the slots 13.

After hardening of the barrier layer, the region in which the depot 3 is situated is sealed in gas-tight manner. The seal is broken by folding open the handle part 54 and pulling the sealing element 52 out of the slots 13. When using the barrier layer, the latter tears, so that then, drawing in the gas that contains nicotine, through the mouthpiece 4, is possible.

In the exemplary embodiment according to FIGS. 13 to 15, the depot 3 is provided with a cylindrical center part, at the two face ends of which the activation device 5 is provided, in each instance, in the form of cutting blades 56. The depot 3 is disposed approximately in the region of the center of the body 1 in the assembled state. In the exemplary embodiment, two sleeves 15 and 16 can be introduced into the body 1. The sleeves 15 and 16 have a membrane 17 and 18, in each instance, on their sides that face one another, which membranes seal off the sleeves 15 and 16, in gas-tight manner, on one side. The sleeves 15 and 16, just like the body 1, are produced from cardboard, plastic, or metal.

The exemplary embodiment according to FIGS. 16 to 18 is configured essentially comparably to the exemplary embodiment according to FIGS. 8 to 12, to the extent that the depot 3, the accommodation 12 including the slots 13, and the mouthpiece 4 are concerned. The activation part 53 is also comparable, whereby the handle piece 54 is eliminated. Disk-shaped sealing elements 57 are provided, which additionally have passage holes 58, in each instance. Furthermore, in the body 1, on the side that lies opposite the slots 13, clearances 19 are configured on the inside. In the assembled state, the sealing elements 57 move into the slots 13. In their sealed position, the sealing elements 57 dip into the clearances 19 only in certain regions. In this position, the activation part 53 is disposed spaced apart from the body 1 by the height "X." At the same time, the passage holes 58 are still located in the region of the slots 13, so that gas passage is prevented. Sealing takes place using the clamping that prevails between the slots 13 and the sealing elements 57, which clamping already brings about sufficient sealing. In addition, however, the possibility exists here, too, of injecting a barrier layer immediately before insertion of the sealing elements 57 into the slots 13. After hardening of the barrier layer, the region in which the depot 3 is situated is sealed in gas-tight manner.

Use of the apparatus according to the invention takes place in simple manner: In the exemplary embodiments according to FIGS. 1 to 7, the block-shaped depot 3 is inserted into the basic body 21 from below. Then, in the exemplary embodiment according to FIGS. 1 to 3, closing of the openings 23, 24, and 25 takes place by means of application of the self-adhesive film 55. The depot, which is actually gas-permeable, is sealed in gas-tight manner by means of application of the film. The depot carrier 2 is then inserted into the accommodation 12. To use the cigarette, the depot carrier 2 is removed from the accommodation 12 by the handle plate 22. Then the self-adhesive film 55 is pulled off by pulling on the tab 51, so that the gas that contains nicotine can exit from the depot 3. By turning the depot carrier by 90 degrees and inserting it into the accommodation 12, the possibility exists of drawing in the gas from the depot, together with air, by way of the mouthpiece 4.

The method of procedure in the exemplary embodiment according to FIGS. 4 to 7 takes place comparably to the method of procedure in the case of the exemplary embodiment according to FIGS. 1 to 3, whereby here, the seal of the depot carrier 2 in the body 1 by means of a press fit or, under some circumstances, by means of application of the barrier layer before insertion of the depot carrier 2 into the accommodation 12. After hardening of the barrier layer, the depot 3 is disposed in the body 1 in gas-tight manner. By means of removing the depot carrier 2, the barrier layer tears, so that the gas can exit from the depot 3. By turning the depot carrier by 90 degrees and subsequently inserting it into the accommodation 12, it is possible to draw the gaseous medium in the depot 3 in through the mouthpiece 4, because in this position, the openings 23 and 24 are oriented coaxial to the body 1, so that suction through the mouthpiece 4 is possible (cf. FIGS. 4 and 5).

In the exemplary embodiment according to FIGS. 8 to 12, assembly first takes place by means of introduction of the depot 3 into the body 1, until the latter has assumed its position between the slots 13 in the region of the accommodation 12. In order to allow precisely positioned and slip-proof positioning, the body 1 can be provided with a diameter narrowing in the region of the accommodation 12, so that the depot 3 is held in the body 1 with slight clamping. Subsequently, the activation device 5 with the sealing elements 52 is inserted into the slots 13. By means of the clamp seat that exists between the slots 13 and the sealing elements 52, sealing has already been brought about in this way. By means of application of an additional barrier layer in the region of the slots 13 and subsequent hardening, here, too, the depot 3, which is actually gas-permeable, is disposed between the sealing elements 52 in gas-tight manner. By means of folding the handle piece 54 open and pulling on the activation device 5, the optionally provided barrier layer tears in the region of the slots 13, so that pulling the sealing elements 52 out is possible. Pulling out the sealing elements 52 eliminates the seal of the depot 3, thereby making it possible to draw in the air and the gas that contains nicotine, for example, through the mouthpiece 4.

In the exemplary embodiment according to FIGS. 13 to 15, placement of the depot 3 in the region of the accommodation 12 of the body 1 also takes place first. Subsequently, the sleeves 15 and 16 can be introduced on both sides of the body 1. After the mouthpiece 4 has been set on, the sleeve 15 projects out of the body 1 (FIG. 13). By pressing in the sleeve 15, the cutting blade 56 that faces the sleeve passes through the membrane 17, so that the gas-tight closure is opened on one side. By further introduction of the sleeve 15 into the body 1, the second cutting blade 56 on the side facing the sleeve 16 also passes through the membrane 18 provided there, so that now, it is possible to draw in air and the gas situated in the depot 3.

In the exemplary embodiment according to FIGS. 13 to 15, placement of components takes place in comparable manner to the exemplary embodiment according to FIGS. 8 to 12, whereby, however, the sealing elements 57 are introduced into the body 1 only in certain regions. Sealing takes place by means of the clamping seat that exists, and can be supported by means of application of a barrier layer. By pressing on the activation part 53, the sealing elements 57 move deeper into the clearances 19. At the same time, the passage holes 58 enter into the center of the body 1 from the wall. As a result, passage of gas is released; drawing the gas in from the depot 3, through the mouthpiece 4, is possible. In the case of additional sealing by means of a barrier layer, this layer is destroyed when pressing on the activation part 53.

The invention claimed is:

1. Apparatus for inhalation of gaseous media, particularly nicotine, which apparatus consists of a sleeve-shaped body (1) and a depot carrier (2) with a handle plate (22) removably disposed in the sleeve-shaped body, the depot carrier (2) accommodating a depot (3) that is sealed in gas-tight manner, and which apparatus has a mouthpiece (4) disposed behind the depot (3) in the suction direction, as well as an activation device (5) for opening the depot (3), whereby the apparatus is refillable, wherein the activation device (5) is formed by a film (55) and the film (55) is self-adhesive, and wherein the activation device (5) comprises a pull-off apparatus which is formed by a tab (51) that projects laterally beyond the handle plate (22) of the depot carrier (2).

2. Apparatus according to claim 1, wherein an accommodation (12) is configured in the body (1).

3. Apparatus according to claim 1, wherein the activation device (5) is formed by an ultra-thin barrier layer.

4. Apparatus according to claim 1, wherein the pull-off apparatus has an activation part (53).

5. Apparatus according to claim 4, wherein a handle piece (54) is disposed on the activation part (53).

6. Apparatus according to claim 5, wherein the handle piece (54) can be folded away.

7. Apparatus according to claim 1, wherein the activation device (5) is formed by at least one cutting blade (56).

* * * * *